United States Patent
Rankin

(10) Patent No.: US 11,311,664 B1
(45) Date of Patent: Apr. 26, 2022

(54) SHAPEABLE INTRAVENOUS TUBING

(71) Applicant: Denicia Dread Rankin, Semmes, AL (US)

(72) Inventor: Denicia Dread Rankin, Semmes, AL (US)

( * ) Notice: Subject to any disclaimer, the term of this patent is extended or adjusted under 35 U.S.C. 154(b) by 0 days.

(21) Appl. No.: 17/227,800

(22) Filed: Apr. 12, 2021

(51) Int. Cl.
*A61M 5/14* (2006.01)
*A61M 39/08* (2006.01)
*A61M 25/00* (2006.01)
*A61M 39/10* (2006.01)

(52) U.S. Cl.
CPC ............ *A61M 5/14* (2013.01); *A61M 25/005* (2013.01); *A61M 39/08* (2013.01); *A61M 39/1011* (2013.01); *A61M 2039/082* (2013.01); *A61M 2039/1083* (2013.01); *A61M 2039/1088* (2013.01)

(58) Field of Classification Search
CPC .... A61M 5/14; A61M 5/1414; A61M 5/1418; A61M 25/005; A61M 39/08; A61M 2039/082; A61M 2205/0266; A61M 2039/0009; A61M 2039/1083; A61M 2039/1088; A61M 39/1011
See application file for complete search history.

(56) References Cited

U.S. PATENT DOCUMENTS

| | | | |
|---|---|---|---|
| 2,377,908 A | 6/1945 | Slaughter | |
| 2,516,930 A | 8/1950 | Varian | |
| 3,618,613 A | 11/1971 | Schulte | |
| 3,910,808 A | 10/1975 | Steward | |
| 4,846,794 A | 7/1989 | Hertzer | |
| 5,853,394 A | 12/1998 | Tolkoff et al. | |
| 6,059,768 A | 5/2000 | Friedman | |
| 6,158,458 A * | 12/2000 | Ryan ..................... | A61J 1/2096 137/515.5 |
| 9,511,185 B2 * | 12/2016 | Slaker ................. | A61M 5/1418 |
| 2002/0040898 A1 | 4/2002 | Von Arx et al. | |
| 2005/0010095 A1 | 1/2005 | Stewart et al. | |
| 2010/0298813 A1 | 11/2010 | Kudo | |
| 2011/0005661 A1 | 1/2011 | Brustad et al. | |
| 2012/0179142 A1* | 7/2012 | Abai ................. | A61M 5/16804 604/537 |
| 2019/0262551 A1* | 8/2019 | Frasnelli ................. | A61M 5/44 |

FOREIGN PATENT DOCUMENTS

| | | |
|---|---|---|
| CA | 1209214 A | 8/1986 |
| WO | 9318813 A1 | 9/1993 |
| WO | 9951153 A3 | 10/1999 |
| WO | 2019108941 A1 | 6/2019 |

OTHER PUBLICATIONS

Shapeable Hose google search screen capture, Mar. 2, 2021.
Silicone Flexible Metal Gooseneck Tubing, Bendable Metal Pine, Product available at Alibaba.com, 2021.

* cited by examiner

*Primary Examiner* — Shefali D Patel
(74) *Attorney, Agent, or Firm* — Gordon & Jacobson, P.C.

(57) ABSTRACT

An intravenous (IV) line set includes a tubing defining a fluid lumen, and first and second connectors attached at opposite ends of the tubing. The tubing is adapted to be formed into a shape and retain the formed shape. In an embodiment, the shape is retained via one or more malleable filaments extending along a length of the tubing. In another embodiment, the shape is retained via magnets.

18 Claims, 4 Drawing Sheets

SHAPEABLE INTRAVENOUS TUBING

BACKGROUND OF THE INVENTION

1. Field of the Invention

The present invention relates to medical conduits. More particularly, the present invention relates to tubular members for administering fluids to a patient.

2. State of the Art

Intravenous (IV) administration sets are well-known for the administration of intravenous therapeutic solutions during a medical treatment. In addition, it is common in the medical industry for patients to simultaneously receive multiple intravenous solutions through intravenous tubing that is coupled together and inserted into the patient's veins or arteries at one or more sites on the body either via peripheral or central venous catheters attached to the patient via percutaneous needle insertion sites. The multiple intravenous tubes are long and can become entangled, intertwined or twisted, making it difficult for medical personnel to determine which medication is flowing through which intravenous tube. Also, the several long tubes can create a messy and complicated working environment, especially during a medical procedure. It is particularly problematic during simple or complex anesthesia when patients are covered and the orientation of their intravenous lines changes as a result of modifying patient positioning (for example from supine to prone) and subsequent draping of various parts of the patient. It is important that the extended intravenous lines do not interfere with treatment during a medical procedure and do not become entangled.

SUMMARY

An intravenous (IV) line set includes a clear, flexible IV tubing, a first connector attached at one end of the IV tubing, and a second connector attached at the opposite end of the IV tubing.

The IV tubing has a proximal end, a distal end, and a fluid lumen extending along the tube from the proximal end to the distal end. The fluid lumen has open proximal and distal ends and is intended to remain open and unkinking along its length for passage of a therapeutic agent. The IV tubing is an extrusion preferably consisting of a single polymer.

The first connector is adapted to connect the proximal end of the IV tubing with a source of liquid therapeutic agent. The second connector is adapted to connect the distal end of the IV tubing to a patient-side connector, such that the first and second connectors are adapted to place the source of liquid therapeutic agent and patient in fluid communication through the IV tubing. Adjacent the distal end of the IV tubing, an injection site is provided through which a bolus of treatment may be administered. The administration set may also include a flow interrupt device structured to a controllably interrupt passage of flow through the IV tubing.

In accord with one aspect of the IV tubing, the IV tubing is adapted to be formed into a shape and retain the formed shape. In one embodiment, one or more malleable filaments extend along the length of the IV tubing. The filament is preferably a wire, and more preferably made of aluminum, copper, silver, steel, or iron or another metal or metal alloy that is adapted to be hand-pliable and also adapted to hold its shape without significant springiness or resilience toward prior form. The malleable filament allows the tubing to be self-retained in a coil, and then manually straightened or otherwise shaped as required to extend between a source and a destination without creating tension between the source and destination.

In accord with another embodiment, the IV tubing has a plurality of magnets extending along the length of the IV tubing. When the IV tubing is helically coiled, the magnets are aligned with each other along the periphery of the coil when the coil has a diameter of three or more inches. The magnets are arranged such that when the IV tubing is in a tightly held coiled arrangement, such arrangement is held. However, the magnets are sufficiently weak such that the IV tubing can be manually uncoiled to extend the first and second connectors as the IV tubing between the source location and the destination, such as a patient. Further, the magnets are sufficiently weak such that when the coil is uncoiled, adjacent magnets do not have any operative effect on each other when more than three inches away from each other. Thus, there is no substantial spring-like effect from pulling the intravenous line apart. After the intravenous line is connected at its proximal distal ends, the extra intravenous line can be re-coiled via attraction of the magnets to obtain an orderly working environment for medical personnel. Such re-coil of the intravenous line can be configured about medical equipment to secure and stabilize the location of the intravenous line during the procedure and recovery. The embodiment may be combined and utilized together.

DETAILED DESCRIPTION OF THE PREFERRED EMBODIMENTS

Figure 1:
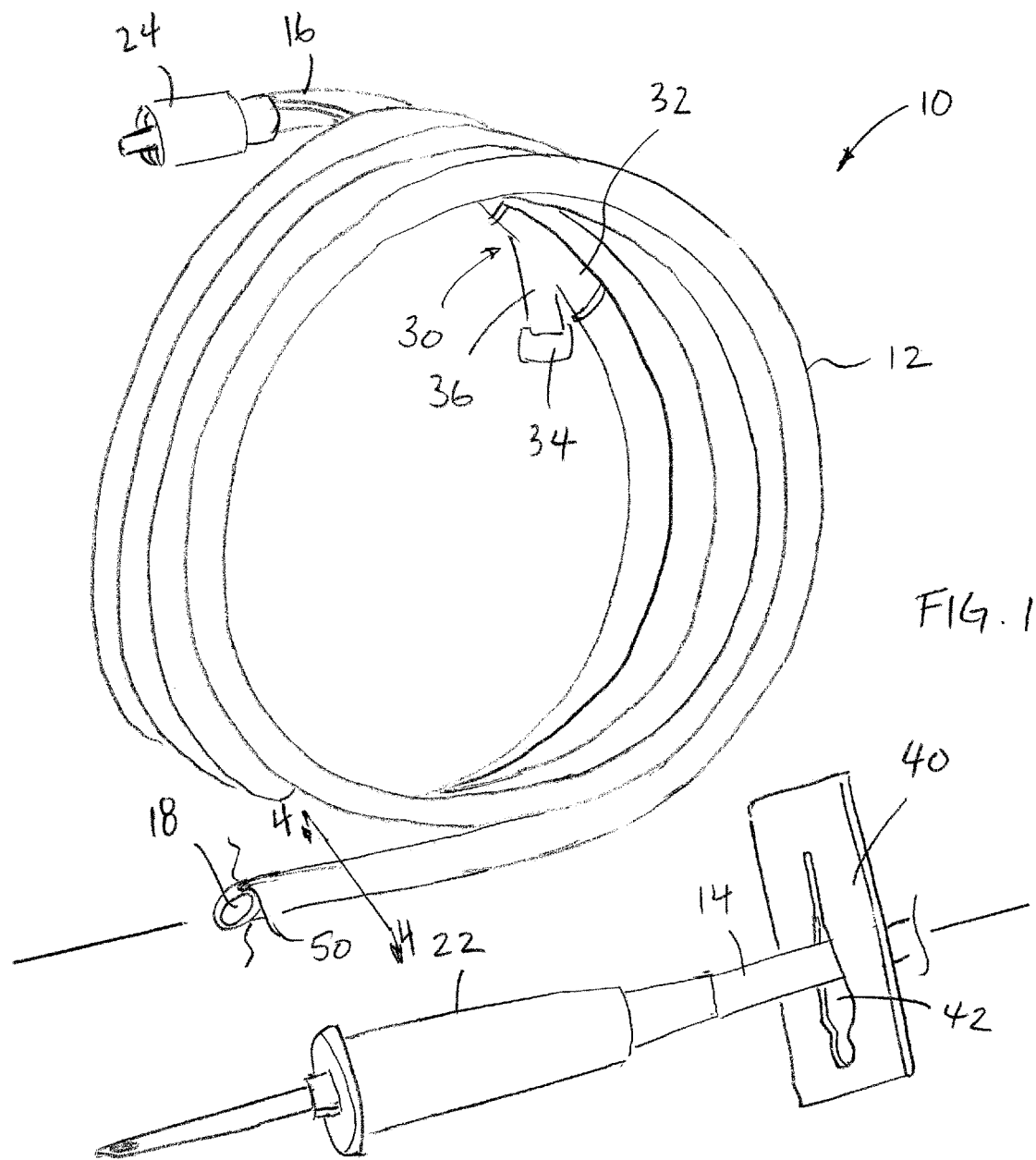
FIG. 1 is a perspective view of an intravenous line set.
Figure 2:
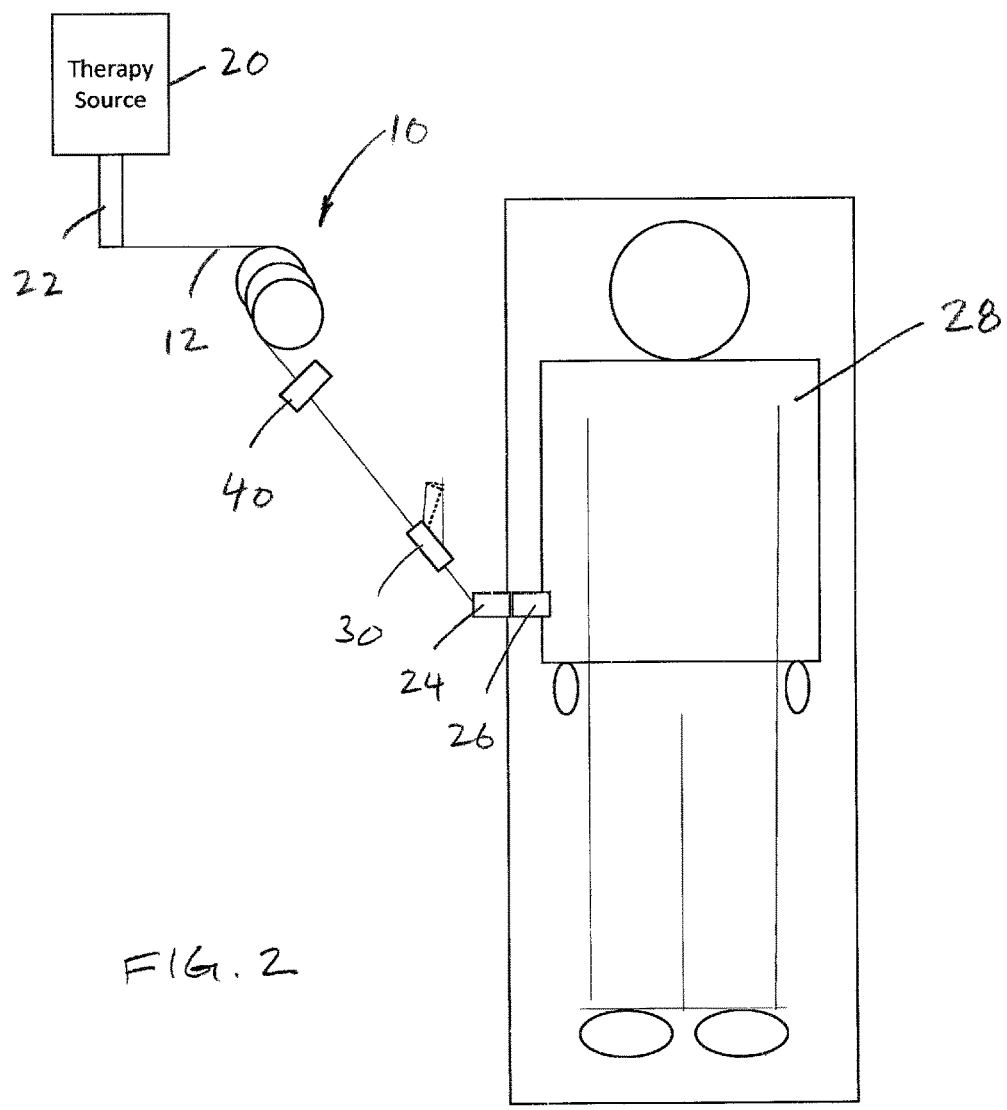
FIG. 2 is a schematic view of the intravenous line set extending between a therapy source and a patient.

Referring now to FIGS. 1 and 2, an intravenous (IV) line set 10 is shown. The IV line set 10 includes a clear, flexible IV tubing 12 having a proximal end 14, a distal end 16, and a fluid lumen 18 extending along the IV tubing from the proximal end to the distal end. The fluid lumen 18 has open proximal and distal ends and is adapted to remain unobstructed and unkinking along its length for delivery of a therapeutic agent from a source 20 therethrough to a patient 28 or other destination (FIG. 2). As described below, the fluid lumen 18 may be situated centrally or axially offset within the IV tubing. Exemplar types of therapeutic agents for delivery through the IV line set, depending on a patient's condition or treatment, may include, an active medication, an anesthetic, a saline solution, or other medically-recommended agents in fluid form. The source may include a bag filled with the treatment and delivered under gravity feed, a filled syringe injected under manual force, a powered pump, or any other suitable source and method for delivery of a therapeutic agent in fluid form.

A first connector 22 is fixed to the proximal end 14 of the IV tubing 12, and a second connector 24 is fixed to the distal end 16 of the IV tubing. The first connector 22 is adapted to connect the proximal end of the IV tubing with the source 20 of liquid therapeutic agent. The second connector 24 is adapted to connect the distal end of the IV tubing to a patient-side connector 26, such that the first and second connectors 22, 24 are adapted to place the source 20 of liquid therapeutic agent and patient 28 in fluid communication through the IV tubing 12. The first connector 22 may be a universal coupling, such as a luer connector, or it may be a well-known universal spike (shown) for insertion into a septum of a medical bag and controlled-release of the contents therefrom. The second connector 24 is preferably a universal coupling.

Adjacent the distal end 16 of the IV tubing, an injection site 30 is provided. The injection site 30 is a Y-connector interposed between and connecting two portions of the IV tubing 12 at one branch 32 of the Y-connector, and a pierceable septum 34 provided at another branch 36 of the Y-connector for administration of a bolus of a therapeutic agent via an injection needle into the IV tubing. (The two portions of the IV tubing together comprise and define one and the same IV tubing for purposes of the description and claims herein.)

The administration set 10 may also include a flow interrupt device 40 provided to a portion of the IV tubing 12. The flow interrupt device 40 is structured to controllably interrupt passage of flow through the IV tubing. In one embodiment, the flow interrupt device 40 is a unitary piece of plastic material having tapered slot 42 with a largest diameter greater than the outer diameter of the IV tubing 12, and a smallest diameter smaller than the outer diameter of the IV tubing 12. The interrupt device is movable relative to the IV tubing to position the slot over IV tubing to permit full flow or to cause the interrupt device 40 at the reduced diameter portion of the slot 42 to crimp the IV tubing 12 and partially or completely interrupt flow through the IV tubing 12.

Figure 3:
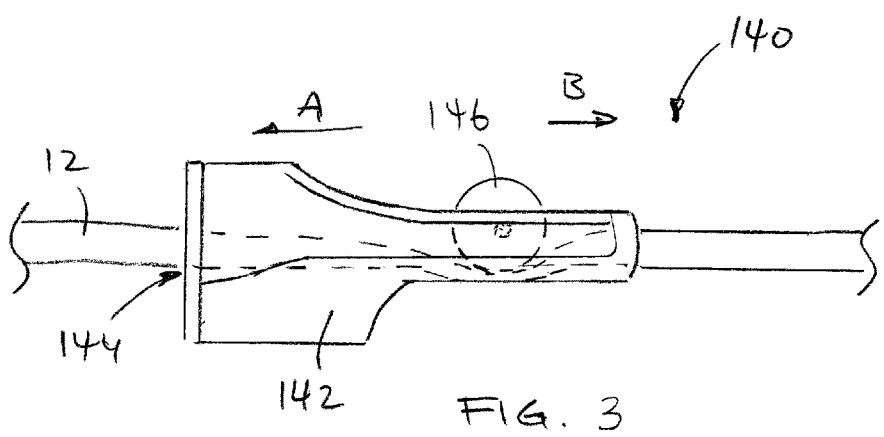
FIG. 3 is a partially transparent view of an alternate flow interrupt device for the intravenous line set.

Turning to FIG. 3, in another embodiment, the flow interrupt device 140 includes multiple components that operate together to adjust the size of a passage for the IV tubing. By way of example, the flow interrupt device 140 can include a carrier 142 defining a passage 144 for the IV tubing 12, and a wheel 146 mounted to the carrier and adapted to change the size of the passage as the wheel is rotatably moved within and relative to the carrier 142. When the wheel 146 is in a first position on the carrier 142 (rotated towards A), the passage 144 is sized to receive the IV tubing 12 without interrupting flow through the IV tubing; when the wheel 146 is rotated into a second position (rotated towards B), the passage 144 is reduced in size to cause the IV tubing 12 within the carrier to be crimped and fluid passage through the IV tubing to be reduced or even prevented.

Referring back to FIG. 1, the IV tubing 12 is an extrusion preferably consisting of a single polymer. In preferred embodiments, the IV tubing 12 is made from standard materials for IV tubing, such as polyvinylchloride (PVC), polyethylene, or polypropylene plastic. If the IV tubing is made from PVC, the IV tubing is softened with plasticizers to render it flexible. The IV tubing 12 preferably has an outer diameter of 2.5-4.0 mm, and more preferably 2.8-3.6 mm, a lumen diameter of 2.0-3.0, and more preferably 2.6-2.8 mm—and a wall thickness of 0.25-1.0 mm between the fluid lumen 18 and the outer surface of the IV tubing.

In accord with one aspect of the IV tubing 12, the IV tubing is adapted to be formed into a shape and then self-retain the formed shape. A preferred shape is a coil. In accord with another aspect, a portion (or all) of the IV tubing is adapted to be deformed from the formed shape and self-retain in a new shape, including the shortest path between the remainder of the coil and the medication source and/or the remainder of the coil and another destination, such as the patient. More particularly, the IV tubing 12 is non-resilient such that the strained IV tubing is not adapted to re-coil or otherwise substantially recover its size and/or shape after deformation. For purposes herein, the following non-exclusive limited meet the definition of "non-resilient" in relation to the IV tubing: (i) an inability of a coil of the IV tubing to automatically recover more than 33 percent of its size and/or shape after being subject to the deformation of straightening, and more preferably an inability to recover more than 20 percent of deformation after being straightened; and/or (ii) an inability of a straightened IV tubing, which has subsequently been deformed into a coil of a diameter of 6 inches to resiliently uncoil on its own to a diameter greater than 8 inches or more, and more preferably such an inability to recover more to a diameter of more than 7.5 inches. Such definitions of non-resilient are not intended to be limiting, but rather to provide limited use parameters of two situations meeting the definition of "non-resilient."

Figure 5:
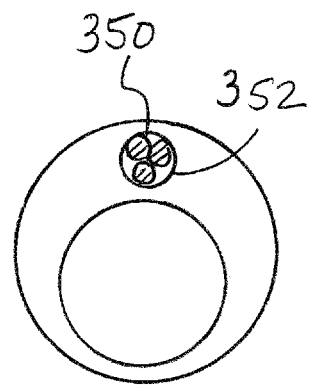
FIGS. 5-7 are other embodiments of the IV tubing of the intravenous line set, as illustrated as cross-sectional views across line 4-4 in FIG. 1.

In one embodiment, the IV tubing includes a malleable filament 50 extending along the length of the IV tubing 12. The filament 50 is preferably a wire, and more preferably made of aluminum, copper, silver, steel, or iron or another metal that is adapted to be hand-pliable and also adapted to hold its shape without significant springiness or resilience toward prior form. Alternatively, the filament 50 is a malleable, shape retaining polymer integrated into the IV tubing. The filament 50 may be co-extruded into the IV tubing, defining a filament lumen 52 at the portion of the tubing polymer receiving the filament. By way of example only, a single filament 50 having a diameter of $\frac{1}{16}$ inch (1.6 mm) to $\frac{1}{128}$ inch (0.20 mm) may be used. Alternatively, referring to FIG. 5, a malleable multi-filamentary construct 350, including discrete parallel filaments, braids, and cables comprised of smaller malleable filaments may be used in a filament lumen 352.

Figure 6:
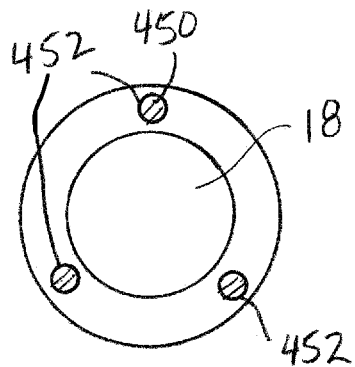
Figure 7:
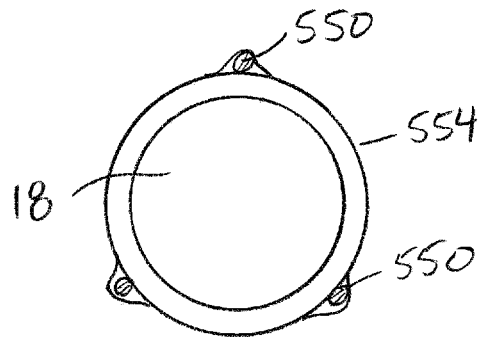

In other embodiments, the filament or filaments may extend parallel to or be wound about the fluid lumen 18. The filament or filaments may extend helically about the fluid lumen 18. Such filaments 450 may extend within multiple filament lumen 452, as shown in FIG. 6, or the filaments 550 may be provided about the exterior 554 of the IV tubing, as shown in FIG. 7. The filaments 50 are preferably substantially small in diameter relative to the diameter of the fluid lumen 18, such that bending of the wire does not result in kinking of the fluid lumen. In preferred embodiments, the shapeable filaments are located below an outer surface of the polymer of the IV tubing, and do not stand proud of the outer surface, and do not require a substantially larger outer diameter than traditional IV tubing. In this manner, the IV tubing from its exterior does not feel different to a health practitioner from non-shapeable IV tubing. This may be important to acceptance of the device into practice.

Figure 8:
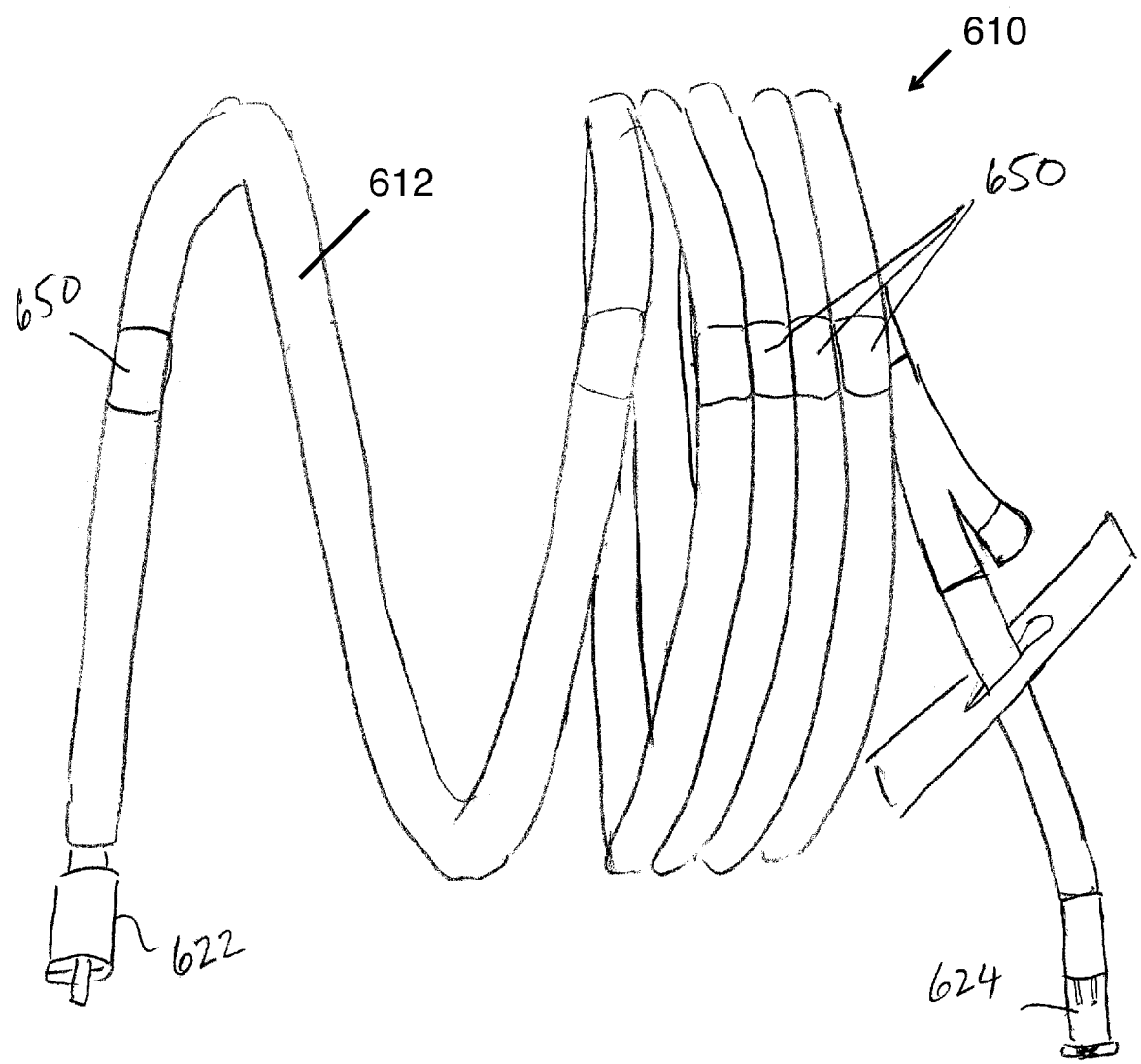
FIG. 8 is a perspective view of another embodiment of an intravenous line set.

Turning now to FIG. 8, another IV administration set 610 is shown. The set is substantially similar to the tubing set 10 described above, with the following differences. First, the first and second connectors 622, 624 are shown as male and female luer connectors, respectively, which similarly can be applied to set 10. In fact, any combination of described universal connectors and spikes can be used in the IV administration sets. Moreover, the IV tubing 612 has a plurality of magnets 650 extending along a periphery of the IV tubing. The magnets can alternatively or additionally be integrated internally within the IV tubing 612. The magnets 650 can be used in the alternative or in addition to the malleable filaments 50, 350, 450, 550. When the IV tubing 612 is helically coiled, the magnets 650 are aligned with each other along the periphery of the coil when the coil has a preferred stored diameter, e.g. three inches. For such a preferred stored diameter, the magnets 650 are preferably spaced 3π inches from each other along the length of the IV tubing. The magnets 650 are arranged such that when the IV tubing is in a tightly coiled arrangement, such arrangement is self-retained. That is, when the IV tubing is coiled, the positive poles of the magnets 650 are adjacent the negative poles of magnets on the adjacent winding of the coil of the IV tubing 612 to retain the coil. However, the magnets 650 are also sufficiently weak such that the IV tubing 612 can be manually uncoiled to extend the first and second connectors 622, 624 between a source of therapeutic agent and a destination, such as a patient. Further, the magnets 650 are sufficiently weak such that when the coil is uncoiled, adjacent magnets do not have any operative effect on each other when more than one to two inches away from each other.

In the above embodiments, no substantial spring-like effect results upon pulling the IV tubing apart. After the IV tubing is connected at its proximal and distal ends to therapy source and patient, the extra IV tubing can be manually re-coiled or formed into a preferred shape and held via attraction of the magnets or deformation of the filament to obtain an orderly working environment for medical personnel. In addition, the IV tubing can be configured about medical equipment to secure and stabilize the location of the intravenous line during a medical procedure and patient recovery.

Figure 9:
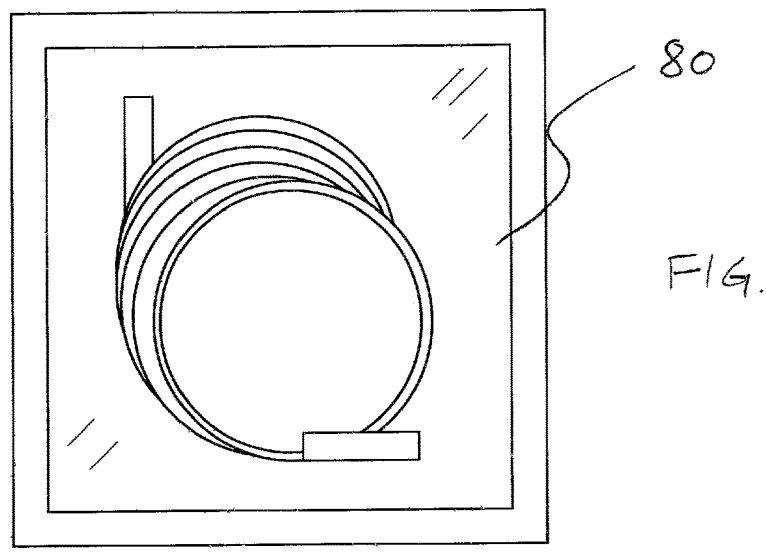
FIG. 9 is packaged sterilized intravenous line set.
Figure 4:
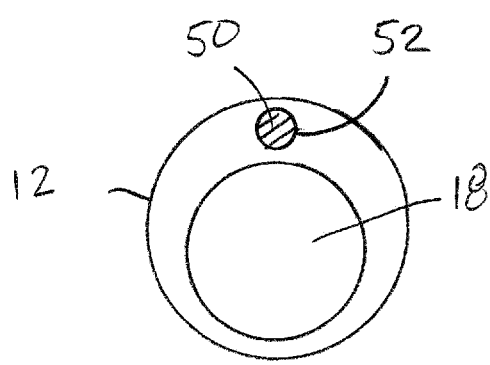
FIG. 4 is a cross-sectional across line 4-4 in FIG. 1.

Turning now to FIG. 9, the IV administration set 10, 610 is preferably provided sterilized in a sealed package 80. The IV tubing of the set is preferably pre-coiled into a compact form within the package 80. In use, the IV tubing of the administration set is removed from the sterile package 80, the first connector is coupled to the medication source, and the second connector is coupled to the patient connector, for example, a needle infusion set inserted percutaneously into a vessel, thereby configuring the IV tubing to deliver fluid therapeutic from the source intravenously to the patient. The IV tubing can be straightened or reshaped at various portions, re-coiled and retained in a coiled configuration, rewrapped upon itself, and/or wrapped and secured upon equipment near the patient without additional equipment. The IV tubing 12 is adapted to retain the formed shape by way of the malleable element extending within or along the tubing or by way of attraction of the magnets magnetically coupling adjacent portions of coiled intravenous line. Thus, after extending the IV administration set between source and destination, the remaining intravenous line can be self-retained in a compact and orderly form suitable for safe and organized medical treatment.

There have been described and illustrated herein several embodiments of an intravenous (IV) administration set and a method of delivering a therapeutic agent to patient through an IV administration set. While particular embodiments of the invention have been described, it is not intended that the invention be limited thereto, as it is intended that the invention be as broad in scope as the art will allow and that the specification be read likewise. Thus, while particular preferred dimensions of the intravenous line, materials for the intravenous line, and types of first and second connectors have been disclosed, it will be appreciated that other dimensions, materials, and connectors can be used as well. It will therefore be appreciated by those skilled in the art that yet other modifications could be made to the provided invention without deviating from its scope as claimed.

What is claimed is:

1. An intravenous (IV) administration set for use between a source of a liquid therapeutic agent and a patient connector attached to a patient, comprising:
    a) a flexible IV tubing for use outside the patient, the IV tubing having a proximal end, a distal end, a length extending between the proximal and distal ends, and a fluid lumen for delivery of the therapeutic agent, the IV tubing being transparent such that when the liquid therapeutic agent is flowing within the fluid lumen, the liquid therapeutic agent is visible from outside the IV tubing,
        at least one shape-retaining element integral to the IV tubing and extending along the length of the IV tubing from the proximal end to the distal end of the IV tubing, the at least one shape-retaining element comprising at least one malleable metal filament co-extruded into the IV tubing;
    b) a first connector adapted to connect the proximal end of the IV tubing with the source of the liquid therapeutic agent; and
    c) a second connector adapted to connect the distal end of the IV tubing to the patient connector, such that the first and second connectors are adapted to place the source of the liquid therapeutic agent and the patient in fluid communication through the IV tubing.

2. The IV administration set according to claim 1, wherein:
    the at least one malleable metal filament consists of a single malleable metal filament.

3. The IV administration set according to claim 1, wherein:
    the at least one malleable metal filament extends helically along the IV tubing.

4. The IV administration set according to claim 1, wherein:
    the at least one malleable metal filament is a plurality of malleable metal filaments.

5. The IV administration set according to claim 1, wherein:
    the at least one malleable metal filament is made of a metal or metal alloy wire.

6. The IV administration set according to claim 5, wherein:
    the metal or metal alloy wire includes aluminum, copper, silver, steel, or iron.

7. The IV administration set according to claim 1, wherein:
    the IV tubing is a construct consisting of both a single polymer and the at least one malleable metal filament.

8. The IV administration set according to claim 7, wherein:
    the single polymer is one of polyvinylchloride (PVC), polyethylene, and polypropylene.

9. The IV administration set according to claim 1, wherein:
    the first connector is one of a spike adapted to pierce a septum and a luer connector, and the second connector is a luer connector.

10. The IV administration set according to claim 9, further comprising:
    a Y-connector attached to the IV tubing proximal of the second connector, the Y-connector including a branch with a pierceable septum for infusion of a bolus of a liquid into the IV tubing between the Y-connector and the second connector.

11. The IV administration set according to claim 10, further comprising:
   a flow interrupt device provided over a portion of the IV tubing to selectively control flow through the IV tubing.

12. The IV administration set according to claim 1, wherein:
   the flexible IV tubing, the first connector, and the second connector are provided sterilized in a sealed package.

13. The IV administration set according to claim 1, wherein:
   the flexible IV tubing has an outer diameter between 2.5-4.0 mm.

14. The IV administration set according to claim 13, wherein:
   the flexible IV tubing has an outer surface, and the at least one shape-retaining element is located below the outer surface.

15. The IV administration set according to claim 13, further comprising:
   a Y-connector attached to the IV tubing proximal of the second connector, the Y-connector including a branch with a pierceable septum for infusion of a bolus of a liquid into the IV tubing between the Y-connector and the second connector; and
   a flow interrupt device provided over a portion of the IV tubing to selectively control flow through the IV tubing.

16. The IV administration set according to claim 15, wherein:
   the flexible IV tubing, the first connector, and the second connector are provided sterilized in a sealed package.

17. An intravenous (IV) administration set for delivery of a liquid therapeutic agent to a patient, comprising:
   a) a flexible IV tubing for use outside the patient, the IV tubing having a proximal end, a distal end, a length extending between the proximal and distal ends, a fluid lumen for delivery of the therapeutic agent, an interior and an exterior, the exterior defining a diameter between 2.5 and 4.0 mm, the IV tubing being transparent such that contents of the fluid lumen are visible to medical personnel through a wall of the IV tubing, the IV tubing made of one of polyvinylchloride (PVC), polyethylene, and polypropylene;
   b) at least one malleable metal filament extending along the length of the IV tubing and incorporated as a part of the IV tubing by being co-extruded into the IV tubing, the at least one malleable metal filament adapting the IV tubing to be non-resilient after deformation along any portion of the length;
   c) a first connector adapted to connect the IV tubing to a source of the liquid therapeutic agent or a mating connector at an upstream location further from the patient; and
   d) a second connector adapted to connect the IV tubing to a mating connector at a downstream location closer to the patient.

18. The IV administration set according to claim 17, wherein:
   the at least one malleable metal filament extends within the interior of the IV tubing.

\* \* \* \* \*